US008334698B2

(12) United States Patent
Tammer et al.

(10) Patent No.: US 8,334,698 B2
(45) Date of Patent: Dec. 18, 2012

(54) SAMPLE HOLDING DEVICE, IN PARTICULAR FOR HOLDING A RODENT OR AN MR PHANTOM IN AN MRT DEVICE

(75) Inventors: Roland Tammer, Bovenden/Harste (DE); Susann Boretius, Gleichen (DE); Thomas Michaelis, Gottingen (DE); Andreas Pucher-Diehl, Gottingen (DE)

(73) Assignees: Max-Planck-Gesellschaft zur Forderung der Wissenschaften e.V. (DE); Biomedizinische NMR Forschungs GmbH (DE)

( * ) Notice: Subject to any disclaimer, the term of this patent is extended or adjusted under 35 U.S.C. 154(b) by 362 days.

(21) Appl. No.: 12/670,888

(22) PCT Filed: Aug. 1, 2007

(86) PCT No.: PCT/EP2007/006820
§ 371 (c)(1),
(2), (4) Date: Feb. 9, 2010

(87) PCT Pub. No.: WO2009/015678
PCT Pub. Date: Feb. 5, 2009

(65) Prior Publication Data
US 2010/0188087 A1 Jul. 29, 2010

(51) Int. Cl.
*G01V 3/12* (2006.01)
*A61B 5/055* (2006.01)

(52) U.S. Cl. ........ 324/321; 324/316; 324/318; 600/417; 600/421

(58) Field of Classification Search .......... 324/300–322; 382/128–133; 600/407–464
See application file for complete search history.

(56) References Cited

U.S. PATENT DOCUMENTS

| 6,275,723 | B1 | 8/2001 | Ferris et al. | |
| 6,873,156 | B2 * | 3/2005 | Ferris et al. | 324/318 |
| 7,378,848 | B2 * | 5/2008 | Gao et al. | 324/318 |
| 7,865,226 | B2 * | 1/2011 | Chiodo | 600/407 |
| 2005/0027190 | A1 | 2/2005 | Chiodo et al. | |

FOREIGN PATENT DOCUMENTS

| EP | 0 947 847 A | 10/1999 |
| EP | 1 746 431 A | 1/2007 |
| WO | WO 94/28431 A | 12/1994 |
| WO | WO 02/32306 A | 4/2002 |
| WO | WO 2007/047149 A | 4/2007 |

* cited by examiner

*Primary Examiner* — Jermele M Hollington
*Assistant Examiner* — Emily Chan
(74) *Attorney, Agent, or Firm* — DLA Piper LLP (US)

(57) ABSTRACT

A sample holding device, adapted for holding a sample, like a rodent or an MR phantom sample in a magnet bore of a magnetic resonance tomography (MRT) device, comprises a sample carrier being adapted for an arrangement in the bore of the MRT device, wherein the sample carrier comprises a carrier platform for accommodating the sample and at least one clamping part with radial locking pieces being adapted for fixing the sample carrier in a hollow enclosure structure, wherein the at least one clamping part is connected with the carrier platform. Furthermore, an MRT device and a method of MRT imaging of a sample are described.

27 Claims, 4 Drawing Sheets

A

B

SAMPLE HOLDING DEVICE, IN PARTICULAR FOR HOLDING A RODENT OR AN MR PHANTOM IN AN MRT DEVICE

RELATED APPLICATION

This is a §371 of International Application No. PCT/EP2007/006820, with an international filing date of Aug. 1, 2007 (WO 2009/015678 A1, published Feb. 5, 2009).

TECHNICAL FIELD

The present disclosure relates to a sample holding device, being adapted for holding a sample, like an animal, in particular rodents, or anon-living test-subject, like an MR phantom in a magnet bore of an magnetic resonance tomography device (MRT device). Furthermore, the present disclosure relates to an MRT device and MR methods using the sample holding device.

BACKGROUND

It is generally known to use magnetic resonance (MR) imaging and spectroscopy for investigating laboratory animals, in particular laboratory rodents, e.g. mice. For MR investigations, the mouse is to be arranged in the magnet bore of an MRT device in an immovable manner. For this purpose, animal holding devices are used, which are adapted for a fixation of the animal in the magnet bore.

FIG. 11 schematically illustrates a conventional prior art animal holding device 100' as it is practically known for laboratory investigations of mice. The animal holding device 100' comprises an carrier platform 310', which is arranged in the magnet bore 210' of an MRT device 200'. The carrier platform 310' is connected and movable with a rail system 250' of the MRT device 200'. The carrier platform 310' accommodates an HF head coil 230' and the mouse 1, which is fixated with a conical receptacle 311' and ear pins 314'. Narcosis gas is flowed to the mouse 1 through the conical receptacle 311'. The HF head coil 230' is arranged above the head 2 of mouse 1. Adjacent to the carrier platform 310', an HF receiver and/or transmitter coil (resonator coil) 240' is arranged.

The conventional animal holding device 100' has a series of disadvantages in terms of conditioning the mouse 1 and providing stable and reproducible measurement conditions. In particular, the disadvantages can be summarized as follows. Firstly, the carrier platform 310' is hanging in a suspended manner. Due to switching of strong magnetic field created in the MRT device 200', mechanical forces can be caused, which result in vibrations or other irregular movements of the carrier platform 310'. These movements essentially impair the MR imaging. As a further disadvantage, the conical receptacle 311' represents a limitation for a close and reproducible positioning of the HF head coil 230' to the mouse head. This disadvantage is even increased with the investigation of small groups of laboratory animals as it is the case e.g. with mice having gene manipulations. While variations of the face and head shapes can be simply compensated by statistical methods with mass investigations of large animal groups, this is impossible with small animal groups. In this case, the HF head coil 230' is to be positioned as close as possible to the mouse head for avoiding influences by the above shape variations.

Furthermore, the conical receptacle 311' does not allow a controlled breathing of the mouse by so-called positive pressure breathing as the receptacle 311' cannot be sealed relative to the mouse head. Accordingly, a positive breathing pressure can not be provided with the conventional animal holding device 100'. Finally, the conventionally used rail system 250' represents a disadvantage in terms of low lateral stability and lack of longitudinal adjustment along the magnet bore 210'. Again, this disadvantage deteriorates the MR imaging quality.

Another disadvantage is given by the fact that the conventional structure does not allow an easy interchangeability of the animal holding device by another holding device accommodating e.g. an MR phantom for reference measurements. The conventional animal holding device represents a special tool exclusively for holding animals. It is not suitable for holding other non-living test-subjects, like a sample container.

Another disadvantage of conventional MRT devices is related to the positioning of the resonator coil 240' in the magnet bore 210'. With conventional practice, the resonator coil 240' is positioned with one of the following techniques. Firstly, the resonator coil can be supported with a construction of radially extending plates connected with axially connected rods. The radially extending plates are fixed in the magnet bore with screws. As the main disadvantage, these screws can be handled only near the opening of the magnet bore. Generally, a resonator coil cannot be stably fixated in an inner part of the magnet bore.

According to a second technique, one of the radially extending plates is replaced by a ring-shaped air-filled hose. The hose can be supplied with pressured air at the positioning site within the magnet bore. However, due to the elasticity of the hose, a stable positioning of the resonator coil is not possible. This disadvantage is even increased during the operation of the MRT device, when the inner volume of the magnetic bore is heated or cooled down.

SUMMARY

An aspect of the disclosure is to provide an improved sample holding device avoiding disadvantages of the conventional techniques. Furthermore, an aspect of the disclosure is to provide an improved MRT device and an improved imaging method.

These aspects are achieved with a sample holding device, an MRT device and an MR imaging method, respectively.

According to a first aspect of the disclosure, the above is achieved by the general technical teaching of providing a sample holding device having a sample carrier with a carrier platform and at least one clamping part, which has radial locking pieces. The carrier platform is extending in a longitudinal direction (z-direction, corresponding to the axial direction of the magnet bore of a MRT device), while the radial locking pieces act in radial directions (perpendicularly relative to the longitudinal extension of the carrier platform). The radial locking pieces are arranged for fixing the sample carrier in an hollow enclosure structure, like e.g. directly in an inner wall of the magnet bore or in an additional component of the sample holding device (slider device, see below). As compared with the conventional techniques, the at least one clamping part allows a self-centring wedge fixation of the sample carrier. Preferably two clamping parts are provided (front and back clamping parts), which are coupled with the longitudinal ends of the area platform. Each of the clamping parts preferably includes at least two, preferably three radial locking pieces forming an interlocking mechanism which securely fixates the sample holding device within the magnet bore of the MRT device. Due to the stable fixation, unintended movements of the animal and associated imaging artifacts can be avoided.

According to a second aspect of the disclosure, the above is achieved by a magnetic resonance tomography (MRT) device including the sample holding device according to the above first aspect and a gradient system device adapted for accommodating the sample holding device within a magnet bore of the MRT device. As an aspect, the MRT device allows a stable positioning of the sample holding device and/or components thereof in the magnet bore. Furthermore, the disclosure provides an improved positioning technique for holding resonator coils in the magnet bore as outlined below. According to various aspects, this improved positioning technique can be implemented as a part of the sample holding device or independently thereof.

According to a third aspect of the disclosure, the above is achieved by a method of MRT imaging of a sample, like an animal, preferably of a rodent, e.g. a mouse or rat or a non-living test-subject wherein the sample holding device is used for holding the sample in the magnet bore of the MRT device.

The carrier platform of the sample holding device generally has a longitudinal extension and a shape selected in dependence on the particular application of the sample carrier and the requirements of the particular measuring conditions. As examples, the carrier platform may have a plane shape or preferably a curved shape (e.g. shape of a half cylinder), which allows to accommodate one sample, like the rodent or the MR phantom, multiple samples, like the rodent and the MR phantom, and/or further components for holding and/or conditioning the sample.

BRIEF DESCRIPTION OF THE DRAWINGS

Further details and aspects of the disclosure are described in the following with reference to the attached drawings, which show in.

DETAILED DESCRIPTION

Figure 1:
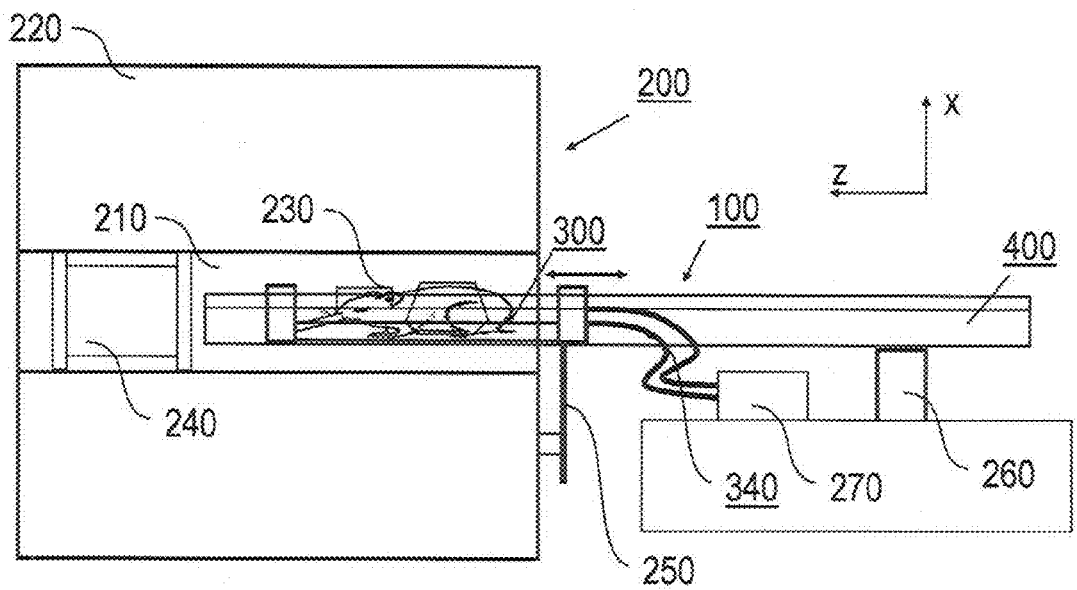
FIG. 1 is a schematic illustration of a first arrangement of the inventive sample holding device arranged in an MRT device, wherein the sample holding device is adapted for holding a rodent.

According to an exemplary arrangement of the disclosure, the sample holding device is adapted for accommodating an animal, e.g. the rodent on the carrier platform. Additionally or alternatively, the sample holding device can be adapted for accommodating a non-living test-subject, like a sample container on the carrier platform. As a particular advantage, the disclosure allows an easy interchangeability of an animal holder or a corresponding MR-phantom holder both being provided with at least one of the clamping parts.

With the animal holding function of the sample holding device, the carrier platform preferably comprises a head fixation part being adapted for fixating the animal head. In this case, advantages for a reproducible arrangement and orientation of the animal on the carrier platform are obtained. Preferably, the head fixation part includes a narcosis tube being arranged for flowing narcosis gas directly into the mouth of the animal. Preferably, the narcotic tube is adapted for the application of an endotracheal tube to the animal. The head fixation part is adapted for clamping the upper jaw of the animal. Advantageously, the head fixation part can fulfill a double function in terms of fixating a part of the animal mouth and flowing narcosis gas directly into the trachea and lungs, thus allowing intermittent positive pressure ventilation (IPPV).

Preferably, the head fixation part includes an adjustment mechanism allowing an adjustment of the head fixation part with regard to at least to directions in space. Advantageously, the head fixation part can be adapted to animals with different sizes and/or head shapes or sizes. Furthermore, this allows a simple adaptation to a head coil of the MRT device, which can be positioned essentially closer to the animal head compared with the conventional techniques.

If according to a further exemplary arrangement of the disclosure, the carrier platform comprises a bottom trough and/or a cover trough holding and/or covering the animal from the lower and/or upper side, respectively, advantages in terms of a more convenient animal holding and conditioning are obtained. The bottom and/or cover trough provide holding surfaces extending along a part of the animal's surface allowing a smooth holding with low forces. According to an exemplary arrangement of the animal holding device, at least one of the bottom trough and the cover trough includes a heating device. Advantageously, the heating device allows maintaining and controlling a physiological temperature of the animal even during experiments extending over some hours. Preferably, the heating device comprises at least one hose circulation, which can be connected with an external thermostat device.

According to a further exemplary arrangement of the disclosure, the carrier platform provides a support for a head coil of the MRT device. Preferably, a head coil receptacle is formed on an upper edge of the carrier platform, e.g. adjacent to the head fixation part. Advantageously, the head coil receptacle provides a predetermined reproducible position of the head coil relative to the position of the mouse on the carrier platform.

With the sample container holding function of the sample holding device, the carrier platform preferably carries a liquid chamber accommodating the test-subject, in particular the sample container. Advantageously, the sample container with a liquid test substance therein can be arranged in a liquid environment in the liquid chamber so that the MR imaging is improved. The liquid chamber can be adapted for accommodating various types of sample containers, like e.g. test tubes. According to a further variant of the disclosure, a temperature control device can be arranged with the liquid chamber on the carrier platform. As an advantage, the temperature of the sample container can be controlled directly with the temperature control device.

According to a further exemplary arrangement of the disclosure, the clamping parts have a structure with a base plate having a ring-shaped form and carrying the radial locking pieces and an insert plate, which can be shifted into an inner space of the ring-shaped base plate, wherein, with a shifting movement of the insert plate towards the base plate, the radial locking pieces are pressed in the radial directions. The insert plate is acting on the radial locking pieces by a mechanical interaction of a peripheral edge of the insert plate with the radial locking pieces. Preferably, at least one of the peripheral edge and an inner surface of a radial locking pieces has a slanted shape so that the radial movement of the radial locking pieces has a smooth characteristic. The coaxial structure of the base and insert plates has the particular advantage of shifting the insert plate into the base plate by only one screw extending in an axial directions through the clamping part. Simply by turning the screw, the base and insert plates can be shifted together so that the radial locking pieces are pressed towards the radial directions.

If according to a further exemplary arrangement of the disclosure a resilient reset member is provided on each of the clamping parts, releasing of the animal holding device is facilitated. The resilient reset member is adapted for shifting the radial locking pieces back to an un-locked position after a separation movement of the base and insert plates.

The clamping parts of the disclosure animal holding device include connectors for at least one of electrical wire connections and hose connections. As an advantage, the connectors allow a mobile application of the animal holding device in particular at various laboratory locations and/or MRT devices. Electrical wire connections can be adapted for connecting the head coil and/or a sensor on the carrier platform with external control devices. Hose connections can be adapted for supplying heating liquid and/or narcosis gas to the carrier platform.

Generally, the sample holding device as characterized above solves the above as the clamping parts allow the stable fixation of the carrier platform in the MRT device. However, particular advantages in terms of flexibility and adaptation to different magnet bore dimensions are obtained if the sample holding device additional comprises a slider device, which provides a counter bearing for the clamping parts, in particular for the radial locking pieces. The slider device has a guide profile accommodating the sample carrier and supporting the animal carrier with at least two opposing radial directions. Preferably, the slider device has a shape of a hollow trough with a bottom wall and sidewalls, which are tilted towards each other at an upper portion opposite to the bottom wall. In this case, the slider device has a simplest structure allowing an access to the carrier platform when the sample carrier is inserted in the slider device. As an alternative, the slider device can have a tube shape.

The MRT device can be equipped with the slider device such that the slider device is arranged in the magnet bore of the MRT device, wherein a part of the slider device can protrude out of the magnet bore. The slider device can be stably supported by a bail extending over the cross-section of the magnetic bore and a further mechanical member, wherein both the bail and the additional mechanical member can be arranged outside the MRT device. This illustration of the disclosure may have advantages in terms of a simple mechanical structure.

However, according to an illustrative example of the disclosure, a support device for supporting the animal carrier, in particular for supporting the slider device is provided, which support device is adapted for being positioned in the magnet bore of the MRT device. Advantageously, with the support device an additional inner support within the MRT device is provided improving the stability and compactness of the animal holding device. To this end, the support device includes a support tube with a socket for supporting the animal carrier and/or the slider device and clamping plate members with radial locking bolts. The clamping plate members are adapted for fixing the support device in the magnet bore of the MRT device. If the support device is used without the animal holding device, the socket can be omitted.

Preferably, the clamping plate member includes a pair of inner and outer plates being arranged with an axial distance on the support tube. The outer plates are connected to each other, e.g. with connecting rods. The radial locking bolts are arranged in a moveable fashion in the circumferential periphery of the outer plates. As an example, three radial locking bolts are arranged with equal angular spacing in each of the outer plates. The inner plates have a smaller diameter compared with the outer plates. Each of the inner plates includes a plurality of mandrels, which are adapted to the number and positions of the radial locking bolts of the outer plates. By introducing the mandrels into the outer plates, the radial locking bolts can be pressed radially outwards. Shifting the mandrels, which preferably have a wedge shape towards the outer plates is obtained by shifting the inner plates to the outer plates, e.g. by a screw connection. Preferably, the inner and outer plates of each clamping plate member are connected with a plurality of hex screws.

Advantageously, the support device provides support not only for the sample holding device, but rather for the resonator coil of the MRT device. For this purpose, the support device includes a resonator coil receptacle connected with the support tube. Preferably, the outer surface of the support tube is the resonator coil receptacle. With this arrangement, the positional relationship of the resonator coil and the animal holding device with the animal on the carrier platform is fixed.

Alternatively, the clamping plate member includes a sleeve member for accommodating the resonator coil and for supporting the support tube and a wheel member for further supporting the support tube. The sleeve member has an adapting effect. As an advantage, the sleeve member allows a fixation of the resonator coil in the magnetic bore of an MRT device even if the inner diameter of the magnetic bore is larger than the outer diameter of the resonator coil.

Further advantages of the MRT device can be obtained if the bail supporting the slider device includes a water level and/or an adjustment device, both of which allowing an adjustment of the position of the slider device in the MRT device. In particular the adjustment device is adapted for adjusting a tilting angle of the animal holding device along the axial direction of the magnet bore.

Further advantages of the disclosure can be summarized as follows. Firstly, the sample holding device with the sample carrier alone or with other of the above components can be completely made of plastic material, like e.g. PEEK (polyetheretherketone), acrylic glass or silicon rubber. Any deterioration of the MR signal by magnetic materials is avoided. The sample holding device allows holding of animals, in particular rodent animals with different sizes, e.g. mice with a weight in the range of e.g. 16 g to 50 g. The sample holding device can be used with other rodent animals as well, e.g. rats. Furthermore, the combination of the support device carrying in particular the resonator coil with the slider device has advantages in terms of charging the MRT device with a rodent animal and providing a counter bearing for the animal carrier.

Furthermore, the support device with the clamping plate members allows a vibrationfree stable positioning of the resonator coil and simultaneously provides an access to the fixation bolts from both sides of the magnet bore. This reproducible positioning has been proposed for the first time. It provides advantages in particular with large MRT devices having an axial length of 2 m or more of the magnet bore.

Illustrative examples of the disclosure are described in the following with reference to the combination of a sample holding device including a sample carrier and a slider device with an MRT device. It is emphasized that the scope of the disclosure is not restricted to this combination but rather may be related to certain components of this combination. In particular, the sample carrier, the combination of the sample carrier with the slider device or the combination of the MRT device with the support device (without the sample holding device) represent independent subjects of the disclosure. Furthermore, the following description refers to an MRT device with a magnet bore axially extending in a horizontal direction (z-direction). The disclosure is not restricted to this particular application. Alternative arrangements of the disclosure can be implemented with an MRT device having another orientation of the magnet bore. Details of the MRT device and the operation thereof are not described here as they are known as such.

FIG. 1 illustrates the sample holding device 100 in combination with the MRT device 200. The sample holding device 100 comprises the sample carrier 300 being further illustrated in FIG. 2 and the slider device 400 being further illustrated in FIG. 4A. The MRT device 200 comprises a magnet bore 210 in a gradient system device 220, a head coil 230, a resonator coil 240 and a bail 250. Components 210 to 240 are provided with a conventional MRT device, like e.g. a Bruker BioSpin B-C 94/30USR with the gradient system device creating a magnetic field of e.g. 9.4 T. Further details of the bail 250 are described below with reference to FIG. 6.

The sample carrier 300 is connected via electrical wire and/or hose connections 340 with an external control device 270, which includes e.g. a control circuit and/or a thermostat device. The slider device 400 is supported on the upper edge of the bail 250 and the further mechanical member 260 outside of the gradient system device 220. With an alternative arrangement, the member 260 can be omitted (see below, FIG. 5).

Figure 2:
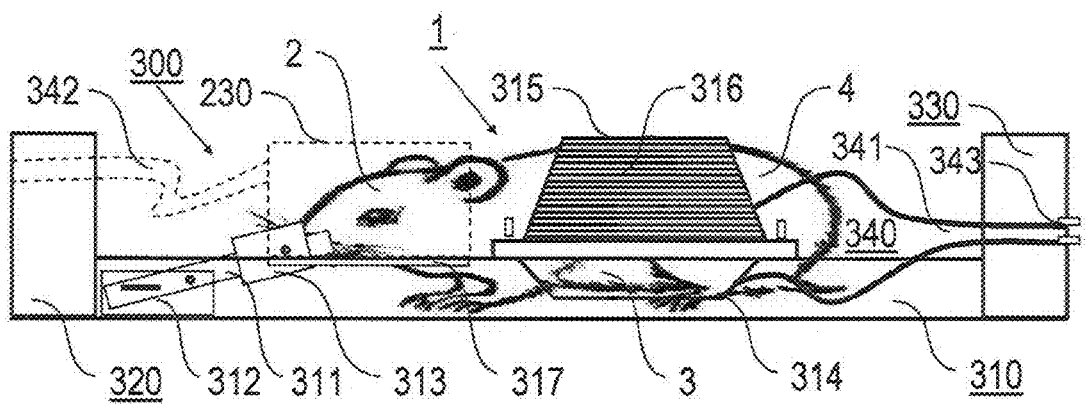
FIG. 2 is an enlarged view of the animal holder illustrated in FIG. 1.

FIG. 2 illustrates further details of the sample carrier 300 being adapted for holding a rodent. The sample carrier 300 comprises a carrier platform 310, a front clamping part 320 and a back clamping part 330. All part of components 310 to 330 are made of plastic, e.g. acrylic glass. The carrier platform 310 has the shape of a half cylinder (diameter about 70 mm), the ends of which being glued with the front and back clamping parts 320, 330 having the same structure. The front and back clamping parts 320, 330 are mirror-inversely connected with the carrier platform 310. Electrical wire and/or hose connections 340 are schematically illustrated with the hoses 341 and the connection lines 342 of the head coil 230. Another hose (not shown) is connected with the head fixation part 311. According to various examples of the disclosure, the connections 340 can be distributed on both front and back clamping parts 320, 330 or combined in one of them.

The carrier platform 310 includes the head fixation part 311 for fixating the head 2 of mouse 1 with the adjustment mechanism 312 being arranged for adjusting a tilting angle of the head fixation part 311 relative to the carrier platform 310 and the axial position of the free end of the head fixation part. In particular, the head fixation part 311 includes a tube with a clip 313, which can be shifted over the mouth of a mouse 1. Via the tube (narcotic tube), a narcotic gas is flowed to the mouse 1.

Furthermore, the carrier platform 310 includes the bottom trough 314 and the cover trough 315 both being connected with the upper edge of the carrier platform 310. The bottom and cover troughs 314, 315 form a receptacle for the body of mouse 1, in particular the mouse venter 3 and mouse back 4. Both troughs include a heating device for controlling the temperature of mouse 1 during MR imaging, like e.g. the hose system 316 being connected via hoses 341 with the external thermostat.

In the neighborhood of a free end of the head fixation part 311, the upper edge of the carrier platform 310 forms a head coil receptacle 317 accommodating the head coil 230 (shown with dashed lines) of the MRT device 200. For imaging another part of mouse 1, the head coil receptacle 317 can be provided at another location along the longitudinal extension of the carrier platform 310.

The dimensions of the sample carrier 300 can be selected in dependence on the requirements of a particular arrangement of the disclosure and in particular in dependence on the inner diameter of the resonator coil. As an example, the axial length (z-direction) is selected in the range of 30 cm to 50 cm, e.g. 40 cm, while the diameter (radial direction, in x-y-plane) is selected in the range of 5 cm to 10 cm, e.g. 6 cm to 7 cm.

Figure 3:
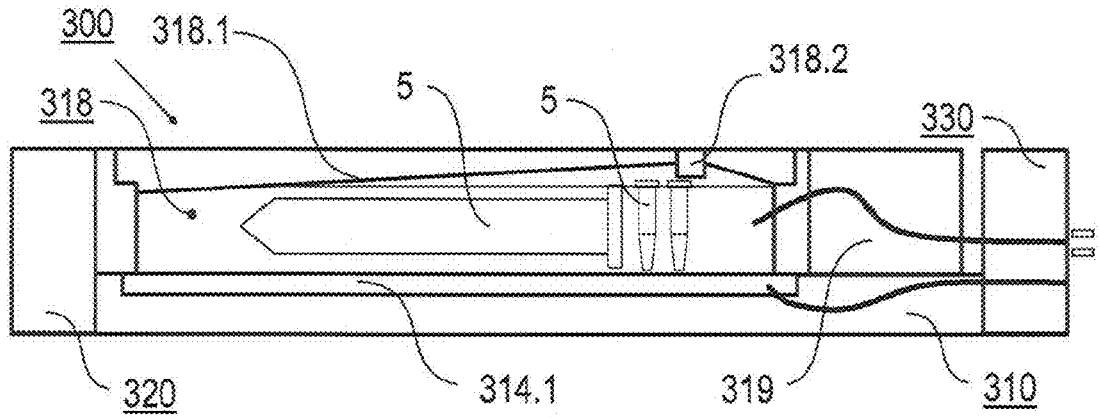
FIG. 3 is an enlarged view of a second arrangement of a sample holding device being adapted for holding a sample container.

FIG. 3 illustrates details of the sample carrier 300, which according to a second arrangement of the disclosure is adapted for accommodating a test-subject, like one or more sample containers 5. As the sample carrier 300 of FIG. 2, the second arrangement also comprises a carrier platform 310, a front clamping part 320 and a back clamping part 330. These components are provided essentially with the same features as described with reference to the remaining figures.

For holding a sample container 5, a liquid chamber 318 is arranged on the carrier platform 310. The liquid chamber 318 is made of a plastic material. It comprises an upper lid 318.1 with a plug 318.2. The components 318.1 and 318.2 can be used for introducing the sample container 5 or the liquid into the liquid chamber 318. The liquid chamber 318 is placed on a heating device 314.1, which is integrated into the carrier platform 310. The heating device can be controlled with a temperature control device 319, which is arranged on the carrier platform 310 as well. Additionally, a local coil (not shown in FIG. 3) can be arranged on the carrier platform 310 in the neighborhood of the liquid chamber 318 (in particular near the sample container 5).

In the liquid chamber, frame parts for fixing the sample container are provided. The geometry (shape, size) of the frame parts is selected in dependency on the sample container 5 to be used. As examples, at least one of the following test tubes can be arranged in a liquid chamber 318: test tubes with a volume of 50 ml or 15 ml or even smaller test tubes (so-called "Eppendorf tubes") can be arranged in the liquid chamber 318. The sample container(s) is/are arranged in a liquid environment, which is provided e.g. by water in the liquid chamber 318.

Figure 4:
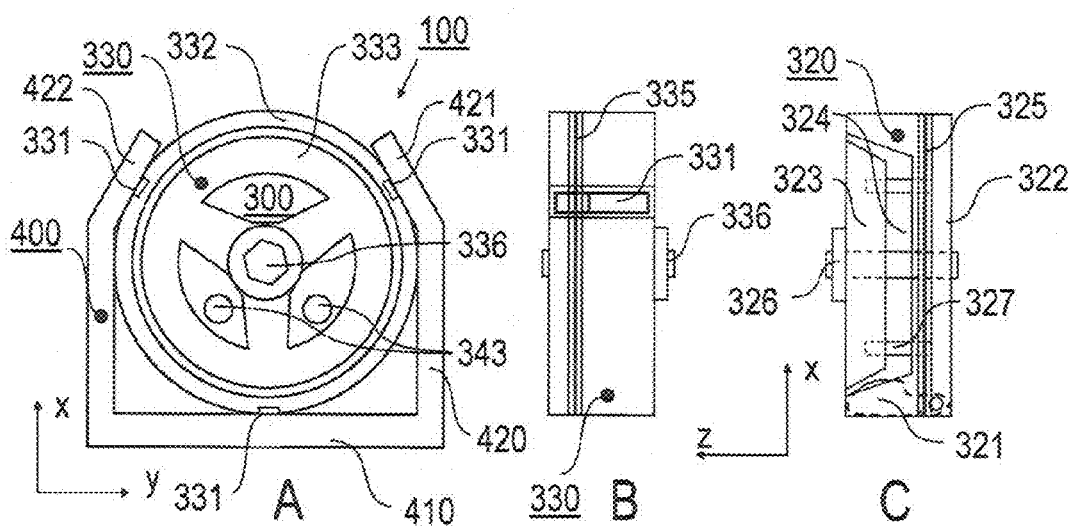
FIGS. 4A to 4C are enlarged views of the animal holding device (A) and the clamping parts (B, C) of the animal carrier thereof.

FIG. 4A illustrates a plane view of the sample holding device 100 (view on x-y-plane) with the sample carrier 300 and the slider device 400. The slider device 400 comprises a plane bottom wall 410, plane side walls 420 and tilted portions 421, 422 of the sidewalls 420. Bottom and side walls 410, 420 are arranged such that the slider device 400 forms a hollow enclosure structure accommodating the sample carrier 300 and forming the counter hearing for all radial locking pieces 321, 331 (see FIGS. 4B, 4C) arranged in the circumferential periphery of the base plate 332.

Furthermore, FIG. 4A shows one of the clamping parts, e.g. the back clamping part 330 comprising a base plate 332, an insert plate 333 being connected with a hex screw 336, and connectors 343 for connecting hoses 341 (see FIG. 2). FIG. 4B illustrates a side view of the back clamping part 330 with the essentially ring shaped base plate 332 and the radial locking piece 331. As a resilient reset member 335, the outer surface of the base plate 332 is surrounded by a rubber ring. The rubber ring pushes the radial locking pieces back into the surface of a clamping part 330 as long as the insert plate 333 does not exert a radial pressure on the radial locking pieces.

FIG. 4C is a further side view (partly in cross-section, partly as a phantom view) illustrating further details of one of the clamping parts, e.g. the front clamping part 320. Like the back clamping part, the front clamping part 320 comprises the base plate 322 and the insert plate 323 being connected with the hex screw 326. Furthermore, guide pins 327 are arranged for adjusting the relative positions of the base and insert plates 322, 323.

The base plate 322, 332 as a ring shape. The radial locking pieces 321, 331 are arranged in the outer surface of the base plate 322, 332. The radial locking pieces 321, 331 can be tilted from a release state (illustrated FIG. 4C) into a clamping state in which the radial locking pieces are protruding from the outer surface of the base plate 322. Tilting movement is caused by shifting the insert plate 323 into the inner space 324 of the base plate 322. As the insert plate 323 has a slanted outer edge 325, the radial locking pieces 321 are pressed in radial direction. Advantageously, this clamping action can be conducted simply by screwing the hex screw 326.

Figure 5:
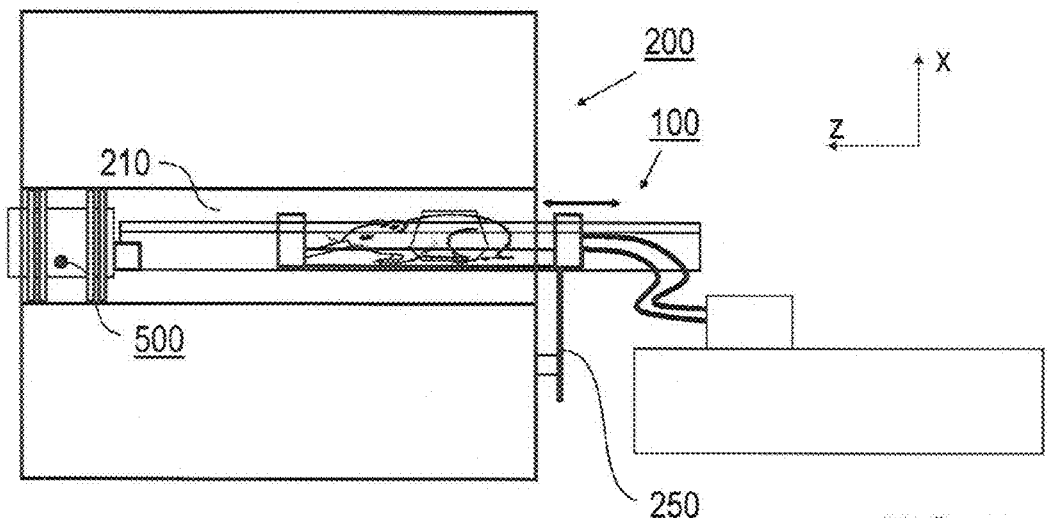
FIG. 5 is a schematic illustration of a further arrangement of a sample holding device in combination with a support device.
Figure 6:
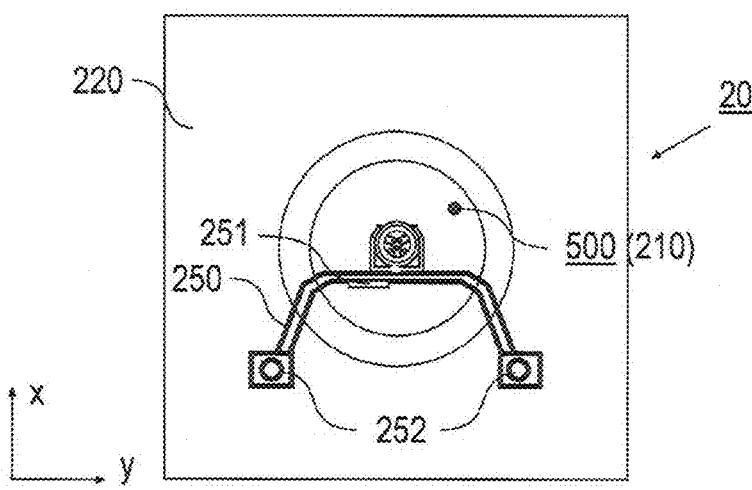
FIG. 6 is a schematic axial view of an exemplary arrangement of an MRT device.

FIG. 5 illustrates a further arrangement of the disclosure, wherein the sample holding device 100 is supported by the bail 250 and the support device 500 arranged in the magnet bore 210 of the MRT device 200. The corresponding front view (x-y plane) is illustrated in FIG. 6.

The sample holding device 100 is resting on the bail 250. The orientation of the sample holding device 100 can be adjusted with an adjustment device 252. The adjustment device 252 comprises a combination of two screw connections with slots in vertical parts of the bail 250. The screw connections are coupled with the enclosure of the gradient system device 220 allowing a manual setting of the height (x-direction) and/or tilting (in x-y-plane) of the sample holding device 100 within the magnetic bore 210. For monitoring the orientation of the bail 250, a water level 251 is connected with the horizontal part of the bail 250. Preferably, the water level 251 is integrally sunk in the bail 250. On the horizontal part of the bail 250, a guiding profile (not shown) can be provided which forms a guidance for the bottom wall 410 of the slider device 400 (see FIG. 4A).

Figure 7:
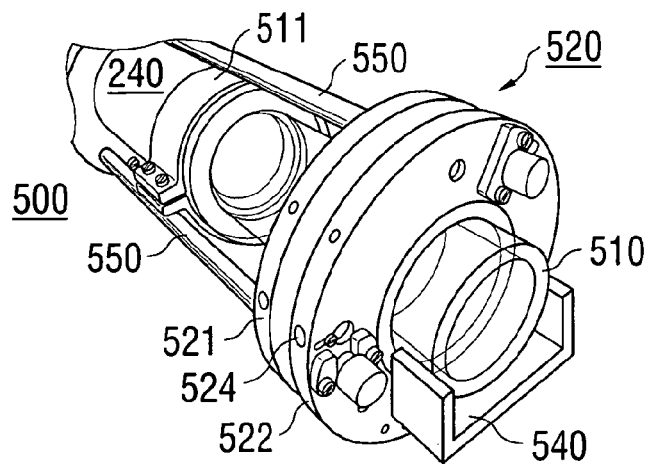
FIGS. 7 to 9 are perspective illustrations showing details of exemplary arrangements of the support device.
Figure 8:
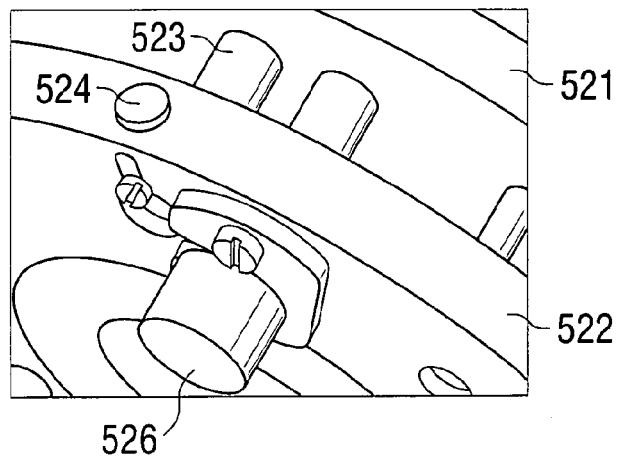
Figure 9:
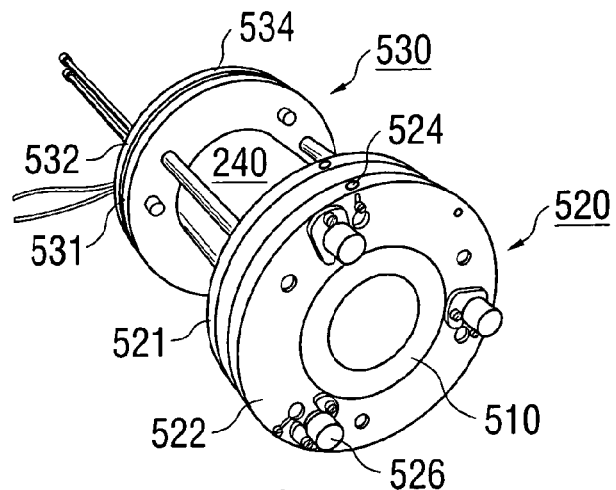

Further details of arrangements of the support device 500 are illustrated in FIGS. 7 to 9. The support device 500 comprises a support tube 510 preferably made of plastic material. At a front end of the support tube 510, a socket 540 for supporting the sample carrier and/or the slider device are arranged. If according to the disclosure the support device 500 is used without the sample holding device, i.e. only for supporting the coil 240, the socket 540 can be omitted.

The support tube 510 carries two clamping plate members 520, 530 (see in particular FIG. 9) with radial locking bolts 524, 534 for fixing the support device in the magnet bore of the MRT device. Each of the clamping plate members 520, 530 includes an inner plate 521, 531 and an outer plate 522, 532. The inner plates have a smaller diameter compared with the outer plates. The pairs of inner and outer plates are arranged with an axial distance on the support tube 510. The inner plates are connected to each other, e.g. with connecting rods 550. Three radial locking bolts 524, 534 are arranged in a radially moveable fashion in the circumferential periphery of each of the outer plates 522, 532. Each of the inner plates 521, 531 includes a plurality of mandrels (e.g. 523, FIG. 8). By shifting the mandrels into the outer plates 522, 532, the radial locking bolts 524, 534 can be pressed radially outwards. Shifting the mandrels, which preferably have a wedge shape towards the outer plates is obtained by screwing the inner plates to the outer plates. Preferably, the inner and outer plates of each clamping plate member are connected with three hex screws 526.

The outer surface of the support tube 510 carries the resonator coil 240. With this arrangement, the relative position of the resonator coil 240 and the animal holding device with the animal on the carrier platform is fixed. FIGS. 7 and 9 differ with regard to the length of the support tube 510 compared with the axial length of the resonator coil 240. For fixing the resonator coil 240 on a longer tube, a clip piece 511 can be provided as shown in FIG. 7.

Figure 10:
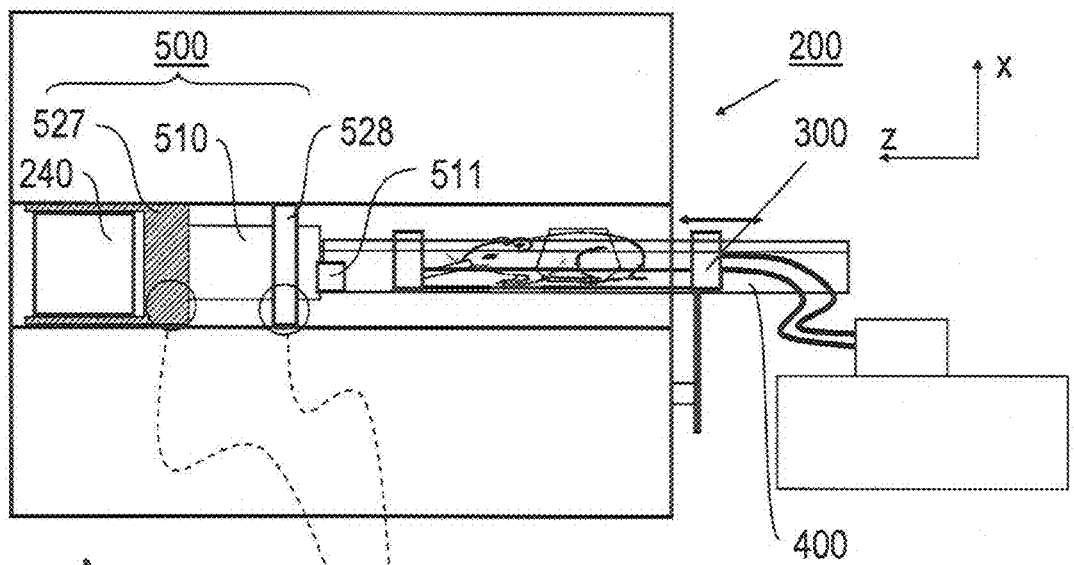
FIGS. 10A and 10B are schematic illustrations of a further arrangement of a sample holding device in combination with a support device.
Figure 11:
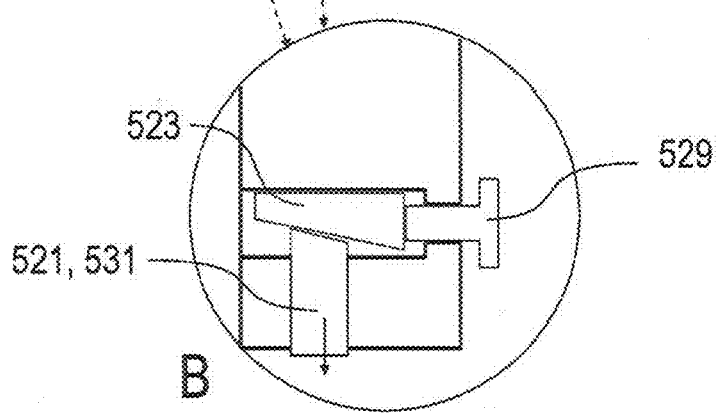
FIG. 11 is a schematic illustration of a conventional animal holding device (prior art).
Figure 11:
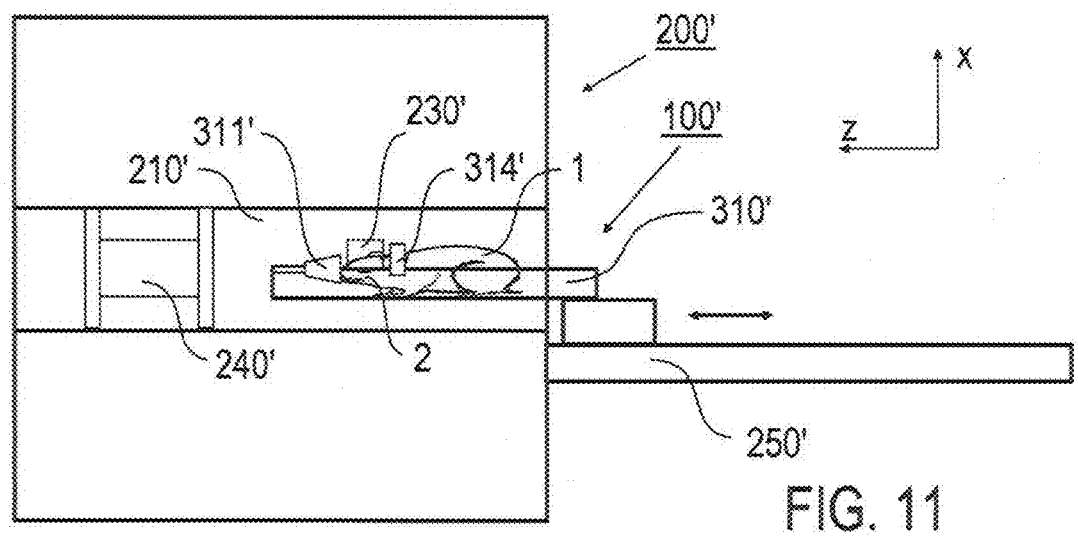

FIGS. 10A and 10B illustrate an alternative arrangement of a support device 500, which is provided for supporting the sample carrier 300 and/or the slider device 400 in the MRT device 200. The support device 500 includes a support tube 510 preferably made of a plastic material. On a first end of the support tube 510, a socket 511 is provided for supporting the animal carrier 300. The other end of the support tube 510 is fixed to a sleeve member 527. The sleeve member 527 comprises a sleeve, which accommodates the resonator coil 240. Furthermore, the support tube 510 carries a wheel member 528, which is positioned on a half portion of the support tube 510 opposite to the sleeve member 527.

Both the sleeve member 527 and the wheel member 528 are clamping plate members having radial locking bolts 521, 531. Further details of the locking mechanism of the members 527, 528 are schematically illustrated in FIG. 10B. The clamping plate members comprise radial locking bolts, which are adapted to be urged radially outwards under the effect of the mandrel 523. The position of the mandrel 523 and accordingly the radial protrusion of the bolt 521, 531 is set with a screw 529, e.g. a hex screw. The members 527, 528 comprise e.g. three locking mechanisms of FIG. 10B, which are arranged on a circumferential periphery of the sleeve member 527 and wheel member 528, respectively.

For MRT imaging, e.g. the mouse 1 is arranged and narcotised on the sample carrier 300 of the inventive sample holding device 100. These steps are conducted outside the magnet bore at a preparation station (not shown). Than, the sample holding device 100 with the mouse 1 is arranged in the magnet bore 210 of the MRT device 200. The sample carrier 300 is shifted with a rod on the slider device 400. Subsequently, the imaging using the MRT device 200 is performed.

The features of the disclosure set forth in the above description, the drawings and the claims can be of significance both individually as well as in combination for the realization of the disclosure in its various forms.

The foregoing examples are provided merely for the purpose of explanation and are in no way to be construed as limiting. While reference to various embodiments are shown, the words used herein are words of description and illustration, rather than words of limitation. Further, although reference to particular means, materials, and embodiments are shown, there is no limitation to the particulars disclosed herein. Rather, the embodiments extend to all functionally equivalent structures, methods, and uses, such as are within the scope of the appended claims.

The invention claimed is:

1. A sample holding device, adapted for holding a sample in a magnet bore of an MRT device, comprising:
    a sample carrier being adapted for an arrangement in the bore of the MRT device, wherein the sample carrier comprises a carrier platform for accommodating the sample, wherein
the sample carrier comprises at least one clamping part comprising:
radial locking pieces being adapted for fixing the sample carrier in a hollow enclosure structure, wherein the at least one clamping part is connected with the carrier platform;
a base plate carrying radial locking pieces, and
an insert plate protruding into an inner space of the base plate and having an outer edge, wherein
the outer edge of the insert plate is arranged for acting on the radial locking pieces, when the insert plate is shifted into the inner space of the base plate.

2. A sample holding device according to claim 1, wherein the at least one clamping part comprises a resilient reset member being arranged for resetting the radial locking pieces.

3. A sample holding device according to claim 1, wherein two clamping parts are provided, which are connected with longitudinal ends of the carrier platform.

4. A sample holding device according to claim 1, wherein a heating device is connected with the carrier platform.

5. A sample holding device according to claim 1, wherein the sample carrier is adapted for accommodating an animal as the sample, and the carrier platform further comprises a head fixation part being adapted for fixating the animal head.

6. A sample holding device according to claim 5, wherein the head fixation part includes an adjustment mechanism being adapted for adjusting the head fixation part in space.

7. A sample holding device according to claim 5, wherein the carrier platform further comprises at least one of a bottom trough and a cover trough each of which forming a receptacle for the animal venter or animal back.

8. A sample holding device according to claim 7, wherein the at least one of the bottom trough and the cover trough includes the heating device.

9. A sample holding device according to claim 1, wherein the sample carrier is adapted for accommodating a sample container as the sample, wherein the carrier platform further comprises a liquid chamber being adapted for accommodating the sample container.

10. A sample holding device according to claim 9, wherein the liquid chamber is arranged on the heating device of the carrier platform.

11. A sample holding device according to claim 9, wherein a temperature control device is arranged on the carrier platform.

12. A sample holding device according to claim 1, wherein the carrier platform further comprises a head coil receptacle arranged on an upper edge of the carrier platform.

13. A sample holding device according to claim 1, further comprising:
a slider device being adapted for supporting the sample carrier in the bore of the MRT device, wherein
the slider device provides the hollow enclosure structure for the radial locking pieces.

14. A sample holding device according to claim 13, wherein the slider device has a hollow trough shape with a bottom wall and side walls, wherein the side walls have upper tilted portions.

15. A sample holding device according to claim 1, further comprising:
a support device being adapted for supporting at least one of the sample carrier and the slider device in the magnet bore of the MRT device, wherein the support device includes
a support tube having a socket for supporting the sample carrier, and
clamping plate members having radial locking bolts being adapted for fixing the support device in the magnet bore.

16. A sample holding device according to claim 15, wherein
each clamping plate member includes a pair of inner and outer plates, wherein
the outer plates are fixedly connected to each other,
the radial locking bolts are movably arranged in the circumferential periphery of the outer plates and
each of the inner plates is arranged for acting on the radial locking bolts, when the inner plate is shifted to the related outer plate.

17. A sample holding device according to claim 16, wherein the inner plates include mandrels with wedge shape being arranged for acting on the radial locking bolts.

18. A sample holding device according to claim 15, wherein the support device further comprises a resonator coil receptacle connected with the support tube.

19. A sample holding device according to claim 15, wherein the clamping plate members comprise a sleeve member being adapted for accommodating a resonator coil and for supporting an end of the support tube, and a wheel member being adapted for supporting another end of the support tube.

20. A magnetic resonance tomography (MRT) device, comprising:
a magnet bore within a gradient system device, and
a sample holding device according to claim 1.

21. A MRT device according to claim 20, further comprising a bail arranged outside the magnet bore for supporting the sample holding device.

22. A MRT device according to claim 21, wherein the bail includes a water level.

23. A MRT device according to claim 21, wherein the bail includes an adjustment device for adjusting a tilting angle of the sample holding device along a longitudinal direction (z) of the magnet bore.

24. A method of MRT imaging of a sample, comprising the steps of:
arranging the sample on an sample carrier of a sample holding device according to claim 1,
arranging the sample holding device with the sample in an magnet bore of an MRT device, and
imaging at least a part of the sample using the MRT device.

25. A method according to claim 24, wherein the sample comprises at least one of an animal and a sample container.

26. A method according to claim 25, wherein the sample is a rodent.

27. A method according to claim 25, wherein the sample is a mouse.

* * * * *